United States Patent [19]

Shoshi et al.

[11] Patent Number: 5,387,487
[45] Date of Patent: Feb. 7, 1995

[54] ELECTROPHOTOGRAPHIC PHOTOCONDUCTOR

[75] Inventors: Masayuki Shoshi, Yokohama; Masakatsu Shimoda, Kurume; Masahiro Taniucchi, Yokohama; Akio Kojima, Mitaka; Masao Yoshikawa; Tetsuro Suzuki, both of Yokohama, all of Japan

[73] Assignee: Ricoh Company, Ltd., Tokyo, Japan

[21] Appl. No.: 936,773

[22] Filed: Aug. 28, 1992

[30] Foreign Application Priority Data

Aug. 30, 1991 [JP] Japan ................. 3-220060
May 13, 1992 [JP] Japan ................. 4-120451

[51] Int. Cl.⁶ .............................. G03G 5/06
[52] U.S. Cl. ......................... 430/58; 430/56; 430/70
[58] Field of Search ............... 430/58, 56, 70

[56] References Cited

U.S. PATENT DOCUMENTS

| | | | |
|---|---|---|---|
| 4,184,871 | 1/1980 | Oba et al. | 430/70 |
| 4,358,521 | 11/1982 | Kondo et al. | 430/83 |
| 4,515,883 | 5/1985 | Sasaki | 430/58 |
| 5,173,384 | 12/1992 | Otsuka | 430/58 |

FOREIGN PATENT DOCUMENTS

| | | | |
|---|---|---|---|
| 53-20334 | 2/1978 | Japan . | |
| 57-201236 | 12/1982 | Japan . | |
| 59-007956 | 1/1984 | Japan | 430/58 |
| 1-287570 | 11/1989 | Japan . | |
| 3-71141 | 3/1991 | Japan . | |

OTHER PUBLICATIONS

"Stilbene", *The Condensed Chemical Dictionary*, G. Hawley, p. 970 (1981).
"Stilbene", Hackh's Chemical Dictionary, J. Grant, p. 639, (1972).

Primary Examiner—Christopher D. Rodee
Attorney, Agent, or Firm—Oblon, Spivak, McClelland, Maier & Neustadt

[57] ABSTRACT

An electrophotographic photoconductor is composed of an electroconductive support, and a photoconductive layer formed on the electroconductive support, which contains a charge generating material and a charge transporting material consisting of an α-cyanostilbene compound of formula (I):

$$R^1-\underset{|}{\overset{CN}{C}}=CH-R^2 \qquad (I)$$

wherein $R^1$ and $R^2$ each represent a phenyl group, a polycyclic aromatic group selected from the group consisting of a naphthyl group, an anthracenyl group, a phenanthrenyl group, and a pyrenyl group, or a heterocyclic group selected from the group consisting of a pyridyl group, a furanyl group, and a quinolyl group.

7 Claims, 2 Drawing Sheets

ELECTROPHOTOGRAPHIC PHOTOCONDUCTOR

BACKGROUND OF THE INVENTION

1. Field of the Invention

The present invention relates to an electrophotographic photoconductor comprising an electroconductive support and a photoconductive layer formed on the electroconductive support, comprising a charge generating material and a charge transporting material consisting of an α-cyanostilbene compound.

2. Discussion of Background

Conventionally, an inorganic photoconductive material such as selenium, selenium-tellurium alloy, or zinc oxide has been widely used for a photoconductive layer of an electrophotographic photoconductor. Recently, studies of electrophotographic photoconductors comprising organic photoconductive materials are made, and some of them are used in practice. Of the above-mentioned organic electrophotographic photoconductors, laminate-type electrophotographic photoconductors are mostly put to practical use, in which photoconductors a photoconductive layer comprises a charge generation layer and a charge transport layer. Owing to such a function-separating photoconductive layer, there is improvement in the photosensitivity and the life span of the photoconductor comprising the organic material, which are conventionally regarded as disadvantageous as compared with the photoconductor comprising the inorganic material. Therefore, the electrophotographic photoconductors comprising the organic photoconductive material have been actively developed, with taking full advantage of the merits of the organic photoconductive material, that is, low cost, safety and diversity.

The above-mentioned laminate-type electrophotographic photoconductor generally comprises an electroconductive support, and a charge generation layer comprising a charge generating material such as a pigment or a dye, and a charge transport layer comprising a charge transporting material such as hydrazone or pyrazoline, which layers are successively overlaid on the electroconductive support. Because the charge transporting material contained in the charge transport layer is an electron-donor material, the above-mentioned photoconductor is of positive-hole-transfer type. Therefore, when the surface of the photoconductor is negatively charged, it exhibits the photosensitivity. However, corona discharge is unstable when used for negatively charging the photoconductor as compared with when used for positively charging the same. The amount of ozone or nitrogen oxides generated in the course of negative charging by the corona discharge is about 10 times that generated in the course of positive charging. Those products are attached to the surface of the photoconductor, so that the photoconductor physically and chemically deteriorates. Furthermore, those products cause the environmental problem.

In addition to the above-mentioned problems, to carry out the development of the negatively-chargeable photoconductor, a positive toner is necessitated. However, from the viewpoint of a triboelectric series, it is difficult to produce such a toner having a positive polarity as can be used with ferromagnetic carrier particles. In a two-component high-resistivity magnetic brush development method, therefore, negatively-chargeable toner is more stable and can be more freely selected and used as compared with the positively-chargeable toner.

In this regard, a positively-chargeable photoconductor is more advantageous and can be more widely used than the negatively-chargeable photoconductor.

With the above-mentioned advantages of the positively-chargeable photoconductor taken into consideration, there are proposed positively-chargeable photoconductors comprising the organic photoconductive materials. For example, it is proposed that a charge transporting material having a high electron-transporting capability such as 2,4,7-trinitro-9-fluorenone be contained in a charge transport layer when the photoconductor is formed by laminating a charge transport layer on a charge generation layer. However, this compound has carcinogenicity, so that the above-mentioned photoconductor is extremely unsuitable for use in practice from the viewpoint of industrial hygiene.

Moreover, U.S. Pat. No. 3,615,414 discloses a positively-chargeable photoconductor comprising a thiapyrylium salt serving as a charge generating material which forms an eutectic complex by combining with polycarbonate serving as a binder resin. However, the above-mentioned photoconductor has the shortcoming that a memory phenomenon tends to occur, and therefore ghost images are easily obtained.

It is possible to prepare a positively-chargeable photoconductor with a laminate-type photoconductive layer in such a configuration that a charge generation layer comprising a charge generating material which can generate a positive hole or electron when the photoconductor is exposed to light, is formed on a charge transport layer which contains a charge transporting material capable of transporting the positive-hole or electron. However, in the above-mentioned structure of the positively-chargeable photoconductor, the charge generation layer becomes a surface layer, so that the charge generating material, which is fragile to external influences, for example, the application of short wavelength light such as ultraviolet light for light exposure, corona discharge, humidity, mechanical friction, inevitably exists in the surface portions of the photoconductor. As a result, electrophotographic properties deteriorate during the preservation of the photoconductor and the image formation process. Consequently, the quality of the obtained images is decreased.

On the other hand, the conventional negatively-chargeable photoconductor comprising a charge transport layer serving as a surface layer formed on a charge generation layer is scarcely subjected to the above-mentioned external influences. Rather, the charge transport layer formed on the charge generation layer has an effect of protecting the charge generation layer.

In the positively-chargeable photoconductor, it is proposed to provide on a charge generation layer comprising a charge generating material a thin protective layer comprising, for example, an insulating, transparent resin to protect the charge generation layer from the aforementioned external influences. However, when the photoconductor is exposed to light, there is a difficulty in efficiently generating electric charges in the charge generation layer because the light applied to the charge generation layer is intercepted by the protective layer. Therefore, the effect of light application is decreased. Furthermore, in the case where the thickness of the protective layer is large, the photosensitivity of the photoconductor deteriorates.

As mentioned above, various proposals for obtaining the positively-chargeable photoconductors have been made, but they have many problems with regard to the photosensitivity, the memory phenomenon or the industrial hygiene.

SUMMARY OF THE INVENTION

Accordingly it is an object of the present invention to provide an electrophotographic photoconductor having high photosensitivity and high durability.

The above-mentioned object of the present invention can be achieved by an electrophotographic photoconductor comprising an electroconductive support and a photoconductive layer formed on the electroconductive support, comprising a charge generating material and a charge transporting material consisting of an α-cyanostilbene compound of formula (I):

$$R^1-\underset{\underset{CN}{|}}{C}=CH-R^2 \quad (I)$$

wherein $R^1$ and $R^2$ each represent a phenyl group; a polycyclic aromatic group selected from the group consisting of a naphthyl group, an anthracenyl group, a phenanthrenyl group, and a pyrenyl group; or a heterocyclic group selected from the group consisting of a pyridyl group, a furanyl group, and a quinolyl group.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
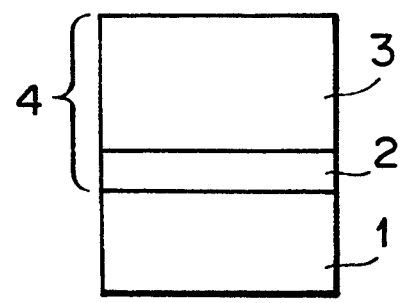
FIG. 1 is a schematic cross-sectional view showing an embodiment of an electrophotographic photoconductor according to the present invention.

An α-cyanostilbene compound used as a charge transporting material in the electrophotographic photoconductor of the present invention is represented by formula (I):

$$R^1-\underset{\underset{CN}{|}}{C}=CH-R^2 \quad (I)$$

wherein $R^1$ and $R^2$ each represent a phenyl group; a polycyclic aromatic group selected from the group consisting of a naphthyl group, an anthracenyl group, a phenanthrenyl group, and a pyrenyl group; or a heterocyclic group selected from the group consisting of a pyridyl group, a furanyl group, and a quinolyl group.

At least one of the phenyl group, the polycyclic aromatic group, or the heterocyclic group represented by $R^1$ or $R^2$ in formula (I) has at least one substituent selected from the group consisting of an alkoxyl group having 1 to 4 carbon atoms such as a methoxy group, an ethoxy group, a propoxy group, or a butoxy group; an alkyl group having 1 to 4 carbon atoms such as a methyl group, a propyl group, a butyl group, or t-butyl group; halogen atom such as fluorine, chlorine, or bromine; a halogenated alkyl group such as a trifluoromethyl group or a trichloromethyl group; an alkoxycarbonyl group having an alkyl group with 1 to 4 carbon atoms such as a methoxycarbonyl group, an ethoxy-carbonyl group or a butoxycarbonyl group; a cyano group; and a nitro group.

Specific examples of the α-cyanostilbene compound of formula (I) for use in the present invention are as follows:

$$R_1-\underset{\underset{CN}{|}}{C}=CH-R_2 \quad (I)$$

| Compound No. | $R_1$ | $R_2$ |
|---|---|---|
| 1 | 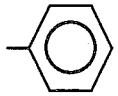 | —NO$_2$ |
| 2 | 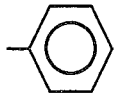 | 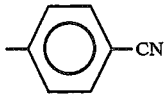—CN |
| 3 | 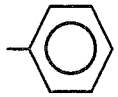 | 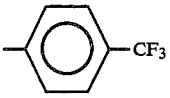—CF$_3$ |
| 4 |  | 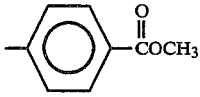—COCH$_3$ (O) |
| 5 |  | —Cl |
| 6 |  | 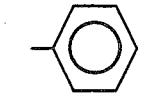 |
| 7 |  | 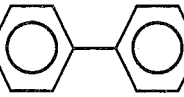 |
| 8 | 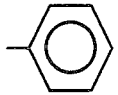 |  |
| 9 | 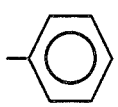 | 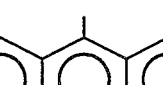 |

-continued $$R_1-\underset{\underset{CN}{|}}{C}=CH-R_2 \qquad (I)$$

| Compound No. | R₁ | R₂ |
|---|---|---|
| 10 | phenyl | methylphenanthrenyl |
| 11 | phenyl | methylpyrenyl |
| 12 | phenyl | 4-methylphenyl-CH₃ |
| 13 | phenyl | 4-methylphenyl-C₂H₅ |
| 14 | phenyl | 4-methylphenyl-C₄H₉ |
| 15 | phenyl | 4-fluorophenyl |
| 16 | phenyl | 2-OCH₃, 4-CN phenyl |
| 17 | phenyl | 2-methylpyridyl |
| 18 | phenyl | 3-methylpyridyl |
| 19 | phenyl | 4-methylpyridyl |
| 20 | phenyl | 2-methylquinolinyl |
| 21 | phenyl | 4-methylquinolinyl |
| 22 | phenyl | 2-OCH₃ methylphenyl |
| 23 | phenyl | 4-OCH₃ methylphenyl |
| 24 | phenyl | 5-methyl-2-nitrofuranyl |
| 25 | 3-CH₃ phenyl | 4-NO₂ phenyl |
| 26 | 3-CH₃ phenyl | 4-CN phenyl |
| 27 | 3-CH₃ phenyl | 4-CF₃ phenyl |
| 28 | 3-CH₃ phenyl | 4-Cl phenyl |
| 29 | 3-CH₃ phenyl | phenyl |
| 30 | 3-CH₃ phenyl | methylnaphthyl |

-continued $$R_1-\underset{\underset{CH}{|}}{C}=CH-R_2 \quad (I)$$

| Compound No. | $R_1$ | $R_2$ |
|---|---|---|
| 31 | 3-methylphenyl | anthracen-9-yl |
| 32 | 3-methylphenyl | phenanthren-9-yl |
| 33 | 3-methylphenyl | pyren-1-yl |
| 34 | 3-methylphenyl | quinolin-4-yl |
| 35 | 3-methylphenyl | 5-nitro-2-furyl (methyl-substituted) |
| 36 | 4-methylphenyl | 4-nitrophenyl |
| 37 | 4-methylphenyl | 4-cyanophenyl |
| 38 | 4-methylphenyl | 4-trifluoromethylphenyl |
| 39 | 4-methylphenyl | 4-chlorophenyl |
| 40 | 4-methylphenyl | phenyl |
| 41 | 4-methylphenyl | naphthalen-1-yl |
| 42 | 4-methylphenyl | anthracen-9-yl |
| 43 | 4-methylphenyl | phenanthren-9-yl |
| 44 | 4-methylphenyl | pyren-1-yl |
| 45 | 4-methylphenyl | quinolin-4-yl |
| 46 | 4-methylphenyl | 5-nitro-2-furyl (methyl-substituted) |
| 47 | 3-chlorophenyl | 4-nitrophenyl |
| 48 | 3-chlorophenyl | 4-cyanophenyl |
| 49 | 3-chlorophenyl | 4-trifluoromethylphenyl |
| 50 | 3-chlorophenyl | 4-bromophenyl |

-continued $$\underset{R_1}{\overset{CN}{\underset{|}{C}}}=CH-R_2 \quad (I)$$

| Compound No. | R₁ | R₂ |
|---|---|---|
| 51 | 3-Cl-C₆H₄– | C₆H₅– |
| 52 | 3-Cl-C₆H₄– | 4-NO₂-C₆H₄– |
| 53 | 3-Cl-C₆H₄– | 3-NO₂-C₆H₄– |
| 54 | 3-Cl-C₆H₄– | 4-CN-C₆H₄– |
| 55 | 3-Cl-C₆H₄– | 4-CF₃-C₆H₄– |
| 56 | 3-Cl-C₆H₄– | 4-Cl-C₆H₄– |
| 57 | 3-Cl-C₆H₄– | C₆H₅– |
| 58 | 3-Cl-C₆H₄– | 1-naphthyl |
| 59 | 3-Cl-C₆H₄– | 9-anthryl |
| 60 | 3-Cl-C₆H₄– | 9-phenanthryl |
| 61 | 4-Cl-C₆H₄– | 1-pyrenyl |
| 62 | 4-Cl-C₆H₄– | 4-quinolyl |
| 63 | 4-Cl-C₆H₄– | 5-nitro-2-furyl |
| 64 | 4-Cl-C₆H₄– | 4-NO₂-C₆H₄– |
| 65 | 4-Cl-C₆H₄– | 3-NO₂-C₆H₄– |
| 66 | 4-Cl-C₆H₄– | 4-CN-C₆H₄– |
| 67 | 4-Cl-C₆H₄– | 4-CF₃-C₆H₄– |
| 68 | 4-Cl-C₆H₄– | 4-Cl-C₆H₄– |
| 69 | 4-Cl-C₆H₄– | C₆H₅– |
| 70 | 4-Cl-C₆H₄– | 1-naphthyl |
| 71 | 4-Cl-C₆H₄– | 9-anthryl |

-continued $$R_1-\underset{\underset{CH-R_2}{\parallel}}{\overset{CN}{C}}\quad (I)$$

| Compound No. | R₁ | R₂ |
|---|---|---|
| 72 | 4-Cl-C₆H₄- | phenanthrenyl |
| 73 | 4-Cl-C₆H₄- | pyrenyl |
| 74 | 4-Cl-C₆H₄- | quinolinyl |
| 75 | 4-Cl-C₆H₄- | 5-nitro-2-methylfuran-yl |
| 76 | 2-F-C₆H₄- | 4-NO₂-C₆H₄- |
| 77 | 2-F-C₆H₄- | 4-CN-C₆H₄- |
| 78 | 2-F-C₆H₄- | 4-CF₃-C₆H₄- |
| 79 | 3-F-C₆H₄- | 4-NO₂-C₆H₄- |
| 80 | 3-F-C₆H₄- | 4-CN-C₆H₄- |
| 81 | 3-F-C₆H₄- | 4-CF₃-C₆H₄- |
| 82 | 4-F-C₆H₄- | 4-Cl-C₆H₄- |
| 83 | 4-F-C₆H₄- | 5-nitro-2-methylfuran-yl |
| 84 | 4-F-C₆H₄- | 4-NO₂-C₆H₄- |
| 85 | 4-F-C₆H₄- | 3-NO₂-C₆H₄- |
| 86 | 4-F-C₆H₄- | 4-CN-C₆H₄- |
| 87 | 4-F-C₆H₄- | 4-CF₃-C₆H₄- |
| 88 | 3-CF₃-C₆H₄- | 4-NO₂-C₆H₄- |
| 89 | 3-CF₃-C₆H₄- | 3-NO₂-C₆H₄- |
| 90 | 3-CF₃-C₆H₄- | 4-CN-C₆H₄- |
| 91 | 3-CF₃-C₆H₄- | 4-CF₃-C₆H₄- |
| 92 | 3-CF₃-C₆H₄- | 4-COOCH₃-C₆H₄- |

-continued $$R_1-\underset{\underset{CH-R_2}{\|}}{C}=CH-R_2 \quad (I)$$
$$\phantom{R_1-}CN$$

| Compound No. | R₁ | R₂ |
|---|---|---|
| 93 | 3-CF₃-C₆H₄- | 4-Cl-C₆H₄- |
| 94 | 3-CF₃-C₆H₄- | C₆H₅- |
| 95 | 3-CF₃-C₆H₄- | 1-naphthyl |
| 96 | 3-CF₃-C₆H₄- | 9-anthryl |
| 97 | 3-CF₃-C₆H₄- | 9-phenanthryl |
| 98 | 3-CF₃-C₆H₄- | 1-pyrenyl |
| 99 | 3-CF₃-C₆H₄- | 4-pyridyl |
| 100 | 3-CF₃-C₆H₄- | 4-quinolyl |
| 101 | 3-CF₃-C₆H₄- | 5-nitro-2-furyl |
| 102 | 4-CF₃-C₆H₄- | 4-NO₂-C₆H₄- |
| 103 | 4-CF₃-C₆H₄- | 3-NO₂-C₆H₄- |
| 104 | 4-CF₃-C₆H₄- | 4-CN-C₆H₄- |
| 105 | 4-CF₃-C₆H₄- | 3-CF₃-C₆H₄- |
| 106 | 4-CF₃-C₆H₄- | 4-COOCH₃-C₆H₄- |
| 107 | 4-CF₃-C₆H₄- | 4-Cl-C₆H₄- |
| 108 | 4-CF₃-C₆H₄- | C₆H₅- |
| 109 | 4-CF₃-C₆H₄- | 1-naphthyl |
| 110 | 4-CF₃-C₆H₄- | 9-anthryl |
| 111 | 4-CF₃-C₆H₄- | 9-phenanthryl |
| 112 | 4-CF₃-C₆H₄- | 1-pyrenyl |

-continued $$R_1-\underset{\underset{CN}{|}}{C}=CH-R_2 \quad (I)$$

| Compound No. | R₁ | R₂ |
|---|---|---|
| 113 | 4-(CF₃)phenyl | pyridin-4-yl |
| 114 | 4-(CF₃)phenyl | quinolin-4-yl |
| 115 | 4-(CF₃)phenyl | 5-nitrofuran-2-yl (methyl-substituted) |
| 116 | naphthalen-1-yl | 4-nitrophenyl |
| 117 | naphthalen-1-yl | 3-nitrophenyl |
| 118 | naphthalen-1-yl | 4-cyanophenyl |
| 119 | naphthalen-1-yl | 4-(CF₃)phenyl |
| 120 | naphthalen-1-yl | 4-(COOCH₃)phenyl |
| 121 | naphthalen-1-yl | 4-chlorophenyl |
| 122 | naphthalen-1-yl | phenyl |
| 123 | naphthalen-1-yl | naphthalen-1-yl |
| 124 | naphthalen-1-yl | anthracen-9-yl |
| 125 | naphthalen-1-yl | phenanthren-9-yl |
| 126 | naphthalen-1-yl | pyren-1-yl |
| 127 | naphthalen-1-yl | pyridin-4-yl |
| 128 | naphthalen-1-yl | quinolin-4-yl |
| 129 | naphthalen-1-yl | 5-nitrofuran-2-yl (methyl-substituted) |
| 130 | 2-cyanophenyl | 4-nitrophenyl |
| 131 | 2-cyanophenyl | 4-cyanophenyl |
| 132 | 2-cyanophenyl | 4-(CF₃)phenyl |

| Compound No. | R₁ | R₂ |
|---|---|---|
| 133 | 2-CN-C₆H₄- | 4-Cl-C₆H₄- |
| 134 | 2-CN-C₆H₄- | C₆H₅- |
| 135 | 2-CN-C₆H₄- | 1-naphthyl |
| 136 | 2-CN-C₆H₄- | 9-anthryl |
| 137 | 2-CN-C₆H₄- | 9-phenanthryl |
| 138 | 2-CN-C₆H₄- | 1-pyrenyl |
| 139 | 2-CN-C₆H₄- | 4-quinolyl |
| 140 | 2-CN-C₆H₄- | 5-nitro-2-furyl |
| 141 | 4-NO₂-C₆H₄- | 4-NO₂-C₆H₄- |
| 142 | 4-NO₂-C₆H₄- | 3-NO₂-C₆H₄- |
| 143 | 4-NO₂-C₆H₄- | 4-CN-C₆H₄- |
| 144 | 4-NO₂-C₆H₄- | 4-CF₃-C₆H₄- |
| 145 | 4-NO₂-C₆H₄- | 4-COOCH₃-C₆H₄- |
| 146 | 4-NO₂-C₆H₄- | 4-Cl-C₆H₄- |
| 147 | 4-NO₂-C₆H₄- | C₆H₅- |
| 148 | 4-NO₂-C₆H₄- | 1-naphthyl |
| 149 | 4-NO₂-C₆H₄- | 9-anthryl |
| 150 | 4-NO₂-C₆H₄- | 9-phenanthryl |
| 151 | 4-NO₂-C₆H₄- | 1-pyrenyl |
| 152 | 4-NO₂-C₆H₄- | 4-quinolyl |
| 153 | 4-NO₂-C₆H₄- | 5-nitro-2-furyl |

-continued $$R_1-\underset{\underset{\text{CH}}{\|}}{\overset{\text{CN}}{C}}=CH-R_2 \quad (I)$$

| Compound No. | R₁ | R₂ |
|---|---|---|
| 154 | 2-pyridyl | 4-nitrophenyl |
| 155 | 2-pyridyl | 3-nitrophenyl |
| 156 | 2-pyridyl | 4-cyanophenyl |
| 157 | 2-pyridyl | 4-(trifluoromethyl)phenyl |
| 158 | 2-pyridyl | 4-(methoxycarbonyl)phenyl |
| 159 | 2-pyridyl | 4-chlorophenyl |
| 160 | 2-pyridyl | phenyl |
| 161 | 2-pyridyl | 1-naphthyl |
| 162 | 2-pyridyl | 9-anthryl |
| 163 | 2-pyridyl | 9-phenanthryl |
| 164 | 2-pyridyl | pyrenyl |
| 165 | 2-pyridyl | 4-quinolyl |
| 166 | 2-pyridyl | 5-nitro-2-furyl |
| 167 | 3-indolyl | 4-nitrophenyl |
| 168 | 3-indolyl | 4-cyanophenyl |
| 169 | 3-indolyl | 4-(trifluoromethyl)phenyl |
| 170 | 3-indolyl | 4-chlorophenyl |
| 171 | 3-indolyl | phenyl |
| 172 | 3-indolyl | 1-naphthyl |
| 173 | 3-indolyl | 9-anthryl |

-continued $$R_1-\underset{\underset{CN}{|}}{C}=CH-R_2 \quad (I)$$

| Compound No. | R₁ | R₂ |
|---|---|---|
| 174 | indole-NH | phenanthrene |
| 175 | indole-NH | pyrene |
| 176 | indole-NH | quinoline |
| 177 | indole-NH | furan-NO₂ |

Of the above-mentioned examples of the α-cyanostilbene compound, the α-cyanostilbene compound of the following formula (II) is preferable for obtaining higher electrophotographic photosensitivity:

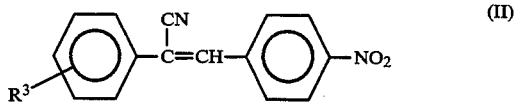

(II)

wherein R³ represents a methyl group, a trifluoromethyl group, or chlorine.

The α-cyanostilbene compound of formula (I) can be obtained by allowing an acetonitrile compound of formula (III) to react with an aldehyde of formula (IV) in the presence of a basic catalyst.

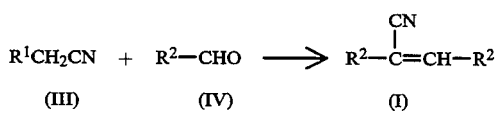

wherein R¹ and R² are the same as those previously defined.

As the basic catalyst, an organic base such as pyridine, piperidine, or triethylamine; a salt of acetic acid such as sodium acetate, potassium acetate or ammonium acetate; an inorganic base such as sodium hydroxide, potassium hydroxide, sodium carbonate or potassium carbonate can be employed.

The above-mentioned reaction for preparing the α-cyanostilbene compound can be carried out without a solvent or in a polar solvent such as methanol, ethanol, tetrahydrofuran, 1,4-dioxane or N,N-dimethylformamide. The reaction is carried out within a temperature range of room temperature to 150° C., preferably room temperature to 100° C.

The α-cyanostilbene compound employed in the electrophotographic photoconductor of the present invention can also be preferably used in the field of electronics as an electronic device such as a solar cell or an organic electroluminescence element.

The structure of the photoconductor of the present invention will now be explained making reference to FIGS. 1 to 3.

A photoconductor shown in FIG. 1 comprises a support 1 and a laminate-type photoconductive layer 4 formed on the support 1 which is an electroconductive support or prepared by providing an electroconductive layer on a sheet. The above photoconductive layer 4 consists of a charge generation layer 2 comprising a charge generating material and if necessary a binder resin, and a charge transport layer 3 formed on the charge generation layer 2, comprising a charge transporting material and if necessary a binder resin.

Figure 2:
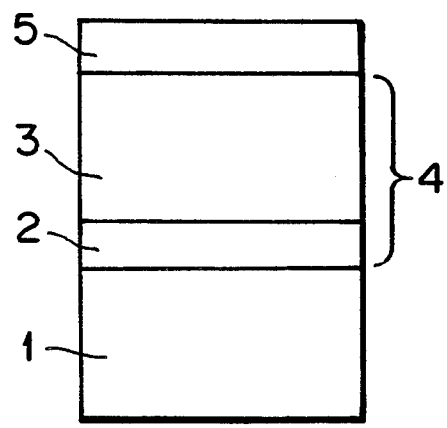
FIG. 2 is a schematic cross-sectional view showing another embodiment of an electrophotographic photoconductor according to the present invention.

The photoconductor shown in FIG. 2 further comprises a protective layer 5 provided on a photoconductive layer 4.

Figure 3:
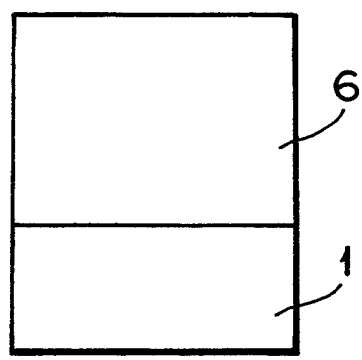
FIG. 3 is a schematic cross-sectional view showing a further embodiment of an electrophotographic photoconductor according to the present invention.

FIG. 3 shows a cross-sectional view of a photoconductor which comprises a single-layered type photoconductive layer 6 formed on a support 1, comprising a charge generating material, a charge transporting material, and if necessary a binder resin. A protective layer can also be provided on the single-layered type photoconductive layer 6, or an intermediate layer may be inserted between the support 1 and the photoconductive layer 4 or 6.

As the charge generating material for use in the photoconductor according to the present invention, any inorganic or organic materials which can absorb visible light and generate free charges can be employed. Specific examples of such materials are inorganic materials such as amorphous selenium, trigonal-system selenium, selenium-arsenic alloy, selenium-tellurium alloy, cadmium sulfide, cadmium selenide, cadmium sulfoselenide, mercury sulfide, lead oxide, lead sulfide, and amorphous silicone; and organic materials such as bisazo dye, polyazo dye, triarylmethane dye, thiazine dye, oxazine dye, xanthene dye, cyanine dye, styryl dye, pyrylium dye, quinacridone dye, indigo dye, perylene dye, polycyclic quinone dye, bisbenzimidazole dye, indanthrone dye, squarylium dye, anthraquinone dye, and phthalocyanine dye.

Specific examples of the binder resin for use in the photoconductive layer are addition polymerization type resins, polyaddition type resins, and polycondensation type resins, such as polyethylene, polypropylene, acrylic resin, methacrylic resin, vinyl chloride resin, vinyl acetate resin, epoxy resin, polyurethane resin, phenolic resin, polyester resin, alkyd resin, polycarbonate resin, silicone resin, and melamine resin; and copolymerization type resins which comprise two or more repeat units in the above-mentioned resins, such as insulating resins of vinyl chloride-vinyl acetate copolymer resin and vinyl chloride-vinyl acetate-maleic anhydride copolymer resin; and polymeric organic semiconductors such as poly-N-vinyl-carbazole.

As the materials for the support of the electrophotographic photoconductor according to the present invention, a sheet, drum or foil of metals such as aluminum and nickel; a plastic film on which aluminum, tin oxide, or indium oxide is deposited; and a film or drum of paper or plastic which is coated by an electroconductive material, can be employed.

When the electrophotographic photoconductor of the present invention comprises a laminate-type photoconductive layer, as shown in FIGS. 1 and 2, the charge transporting material is singly dissolved or dispersed in an appropriate solvent or in combination with an appropriate binder resin to obtain a coating liquid for a charge transport layer. The thus obtained coating liquid is coated on a charge generation layer and dried, so that the charge transport layer is formed on the charge generation layer.

As the solvent used in preparing the charge transport layer, N,N-dimethylformamide, toluene, xylene, monochlorobenzene, 1,2-dichloroethane, dichloromethane, 1,1,1-trichloroethane, 1,1,2-trichloroethylene, tetrahydrofuran, methyl ethyl ketone, cyclohexanone, ethyl acetate, and butyl acetate can be employed.

It is preferable that 20 to 200 parts by weight of the charge transporting material be contained in 100 parts by weight of the binder resin in the charge transport layer. It is also preferable that the thickness of the charge transport layer be 5 to 50 $\mu$m, more preferably 5 to 30 $\mu$m.

In the present invention, the charge generation layer can be formed by vacuum-depositing the charge generating material on the electroconductive support. Alternatively, the charge generating material is dissolved or dispersed in an appropriate solvent singly or in combination with an appropriate binder resin to obtain a coating liquid for the charge generation layer, and the thus obtained liquid is coated on the support and dried.

When the charge generation layer is formed by coating a dispersion of the charge generating material, it is preferable that the average particle size of the charge generating material be within the range from 0.01 $\mu$m to 2 $\mu$m, more preferably 0.01 $\mu$m to 1 $\mu$m.

When the particle size of the charge generating material is 2 $\mu$m or less, it can be uniformly dispersed in the solvent, and part of particles can be prevented from protruding over the surface of the charge generation layer, so that the surface smoothness is not impaired. Therefore, electrical discharge taking place on the particle-protruded portion can be prevented and the toner filming phenomenon does not occur.

In addition, when the particle size of the charge generating material is 0.01 $\mu$m or more, the particles do not tend to aggregate. As a result, an increase of the resistivity of the charge generation layer and a decrease of the photosensitivity of the photoconductor can be prevented, so that the photoconductor can be repeatedly used.

To prepare the charge generation layer, the charge generating material is dispersed in the form of finely-divided particles in the solvent in a ball mill or a homomixer. Then, finely-divided particles of the charge generating material are mixed with a binder resin and dispersed to obtain a coating liquid for the charge generation layer, and the thus obtained coating liquid is coated on the support. In this method of forming the charge generation layer, it is preferable that the particles of the charge generating material be dispersed with the application of supersonic wave thereto so as to obtain a uniform dispersion.

It is preferable that 20 to 200 parts by weight of the charge generating material be contained in 100 parts by weight of the binder resin in the charge generation layer. It is also preferable that the thickness of the charge generation layer be 0.1 to 10 $\mu$m, more preferably 0.5 to 5 $\mu$m.

In the case where the electrophotographic photoconductor of the present invention comprises a single-layered type photoconductive layer, as shown in FIG. 3, it is preferable that 20 to 200 parts by weight of the charge generating material and 20 to 200 parts by weight of the charge transporting material be contained in 100 parts by weight of the binder resin in the photoconductive layer. It is also preferable that the thickness of the single-layered type photoconductive layer be 7 to 50 $\mu$m, more preferably 10 to 30 $\mu$m.

Furthermore, the previously mentioned intermediate layer which can be inserted between the support and the photoconductive layer functions as an adhesive layer or a barrier layer. As the materials for the intermediate layer, the same resins as used in preparing the photoconductive layer as the binder resins, and resins such as polyvinyl alcohol, ethyl cellulose, carboxymethyl cellulose, vinyl chloride-vinyl acetate copolymer, vinyl chloride-vinyl acetate-maleic anhydride copolymer, casein, N-alkoxymethyl nylon can be employed. In addition to the above, tin oxide or indium oxide may be dispersed in one of the above-mentioned resins. A film prepared by deposition of aluminum oxide, zinc oxide, or silicon oxide can also be employed. It is preferable that the thickness of the intermediate layer be 1 $\mu$m or less.

As the materials for the above-mentioned protective layer, the above-mentioned resins are used as they are, or a material having a low resistivity such as tin oxide or indium oxide may be dispersed in the above resins. In addition to the above, an organic plasma polymerization film can be used as the protective layer. In this case, the organic plasma polymerization film may comprise oxygen, nitrogen, halogen, or an atom belonging to the group III or the group V in the periodic table when necessary.

Other features of this invention will become apparent in the course of the following description of exemplary embodiments, which are given for illustration of the invention and are not intended to be limiting thereof.

Synthesis Example 1

Synthesis of 4'-nitro-α-cyanostilbene (Compound No. 1)

A mixture of 3.70 g of commercially available phenylacetonitrile, 4.53 g of commercially available 4-nitrobenzaldehyde, and 3.94 g of anhydrous sodium carbonate was refluxed with stirring in 150 ml of ethanol for 6 hours. After the completion of the reaction, the thus obtained reaction mixture was cooled to room temperature and poured into water. With the addition of 300 ml of toluene, the reaction mixture was satisfactorily stirred. A toluene layer was separated and washed with water until it turned neutral. After the toluene layer was dried over anhydrous magnesium sulfate, toluene was distilled away. The thus obtained residue was subjected to silica gel column chromatography using toluene as a developing solvent. The thus obtained crude product was recrystallized from ethanol, so that 4.08 g of 4'-nitro-α-cyanostilbene (Compound No. 1) was obtained in pure form.

The melting point of the product was 120.5° to 121.0° C.

Figure 4:
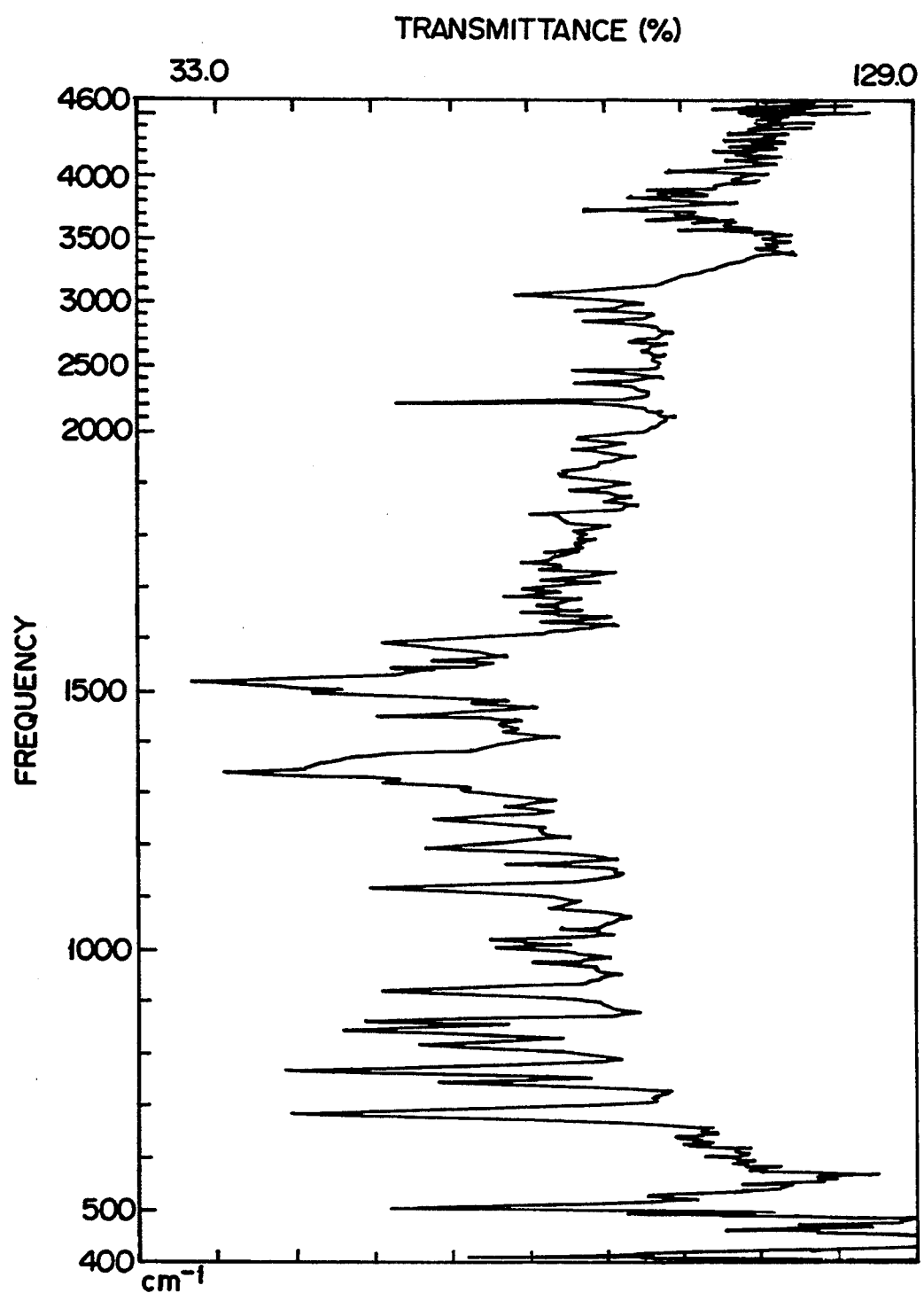
FIG. 4 is an IR spectrum of a compound prepared in Synthesis Example 1.

FIG. 4 shows an IR spectrum of 4'-nitro-α-cyanostilbene.

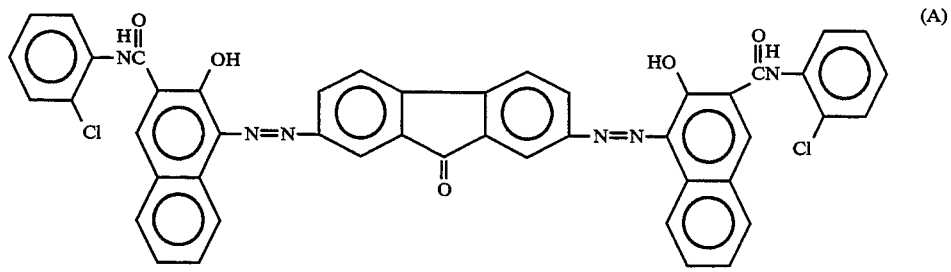
(A)

Synthesis Examples 2 to 36

The procedure for preparing the 4'-nitro-α-cyanostilbene in Synthesis Example 1 was repeated except that phenylacetonitrile and 4-nitrobenzaldehyde used in Synthesis Example 1 were respectively replaced by various kinds of acetonitrile compounds of formula (III) and various kinds of aldehydes of formula (IV), so that α-cyanostilbene compounds shown in Table 1 were obtained in pure form. The melting point and the results of elemental analysis of each product are shown in Table 1.

by weight of tetrahydrofuran were dispersed in a ball mill for 12 hours.

Tetrahydrofuran was further added to the thus obtained mixture in such an amount that the obtained dispersion might have a concentration of 2 wt % and the mixture was dispersed again to prepare a coating liquid for a charge generation layer. The thus obtained coating liquid was coated by a doctor blade on an aluminum-deposited surface of an aluminum-deposited polyester film with a thickness of 100 μm serving as a support, and dried, so that a charge generation layer with a thickness of 1.0 μm was formed on the support.

Formation of Charge Transport Layer

TABLE 1

| Synthesis Example No. | Compound No. | Melting Point (°C.) | Elemental Analysis | | |
|---|---|---|---|---|---|
| | | | C Found (Calculated) | H Found (Calculated) | N Found (Calculated) |
| Example 1 | 1 | 120.5–121.0 | 72.13 (71.99) | 3.96 (4.03) | 11.30 (11.19) |
| Example 2 | 2 | 170.0–171.0 | 83.61 (83.46) | 4.16 (4.38) | 12.16 (12.17) |
| Example 3 | 3 | 113.0–113.5 | 70.47 (70.33) | 3.47 (3.69) | 5.24 (5.13) |
| Example 4 | 5 | 102.0–103.0 | 75.13 (75.16) | 4.07 (4.21) | 5.76 (5.84) |
| Example 5 | 6 | 86.0–86.8 | 87.89 (87.77) | 5.25 (5.40) | 6.73 (6.82) |
| Example 6 | 7 | 150.0–151.0 | 89.76 (89.65) | 5.18 (5.37) | 4.96 (4.98) |
| Example 7 | 8 | 109.5–110.0 | 89.48 (89.38) | 4.98 (5.13) | 5.42 (5.49) |
| Example 8 | 22 | 52.0–53.0 | 81.79 (81.68) | 5.49 (5.57) | 5.93 (5.95) |
| Example 9 | 23 | 94.0–94.8 | 81.52 (81.68) | 5.48 (5.57) | 6.08 (5.95) |
| Example 10 | 25 | 118.3–119.0 | 72.68 (72.72) | 4.61 (4.58) | 10.60 (10.60) |
| Example 11 | 36 | 129.5–130.3 | 72.84 (72.72) | 4.55 (4.58) | 10.65 (10.60) |
| Example 12 | 52 | 136.0–137.0 | 63.15 (63.28) | 3.20 (3.19) | 9.85 (9.84) |
| Example 13 | 54 | 204.5–205.5 | 72.69 (72.60) | 3.56 (3.43) | 10.59 (10.58) |
| Example 14 | 55 | 104.5–105.5 | 62.64 (62.46) | 2.86 (2.95) | 4.54 (4.55) |
| Example 15 | 64 | 170.0–171.0 | 63.38 (63.28) | 2.94 (3.19) | 9.91 (9.84) |
| Example 16 | 66 | 190.0–190.8 | 72.68 (72.60) | 3.26 (3.43) | 10.48 (10.59) |
| Example 17 | 67 | 81.0–82.5 | 62.52 (62.46) | 2.98 (2.95) | 4.66 (4.55) |
| Example 18 | 69 | 113.0–113.5 | 75.20 (75.16) | 4.16 (4.21) | 5.82 (5.84) |
| Example 19 | 88 | 126.0–127.0 | 60.41 (60.38) | 2.79 (2.85) | 8.82 (8.80) |
| Example 20 | 97 | 177.5–178.3 | 77.12 (77.21) | 3.83 (3.78) | 3.75 (3.75) |
| Example 21 | 98 | 123.0–124.5 | 78.70 (78.58) | 3.71 (3.55) | 3.60 (3.53) |
| Example 22 | 102 | 121.0–122.0 | 60.34 (60.38) | 2.72 (2.85) | 8.77 (8.80) |
| Example 23 | 104 | 168.0–169.0 | 63.53 (68.46) | 2.82 (3.04) | 9.38 (9.39) |
| Example 24 | 112 | 205.5–206.5 | 78.37 (78.58) | 3.47 (3.55) | 3.68 (3.53) |
| Example 25 | 116 | 123.5–125.0 | 76.12 (75.99) | 3.95 (4.03) | 9.40 (9.33) |
| Example 26 | 118 | 148.0–149.0 | 85.79 (85.69) | 4.19 (4.32) | 9.85 (9.99) |
| Example 27 | 119 | 131.0–131.5 | 74.41 (74.30) | 3.59 (3.74) | 4.31 (4.33) |
| Example 28 | 141 | 109.0–110.0 | 59.93 (60.02) | 3.22 (3.07) | 14.30 (14.23) |
| Example 29 | 143 | 246.0–247.0 | 69.98 (69.82) | 3.10 (3.30) | 15.31 (15.27) |
| Example 30 | 144 | 130.0–130.7 | 67.04 (67.13) | 2.99 (3.17) | 9.61 (9.79) |
| Example 31 | 147 | 178.5–179.5 | 72.02 (71.99) | 4.10 (4.03) | 11.26 (11.19) |
| Example 32 | 154 | 142.0–143.0 | 67.05 (66.93) | 3.47 (3.61) | 16.71 (16.73) |
| Example 33 | 156 | 151.5–152.3 | 78.02 (77.91) | 3.79 (3.92) | 18.15 (18.17) |
| Example 34 | 157 | 93.5–94.2 | 65.84 (65.70) | 3.20 (3.31) | 10.31 (10.22) |
| Example 35 | 160 | 59.0–60.0 | 81.66 (81.53) | 4.71 (4.89) | 13.58 (13.58) |
| Example 36 | 166 | 202.0–203.0 | 59.61 (59.76) | 2.85 (2.93) | 17.45 (17.42) |

Example 1

Formation of Charge Generation Layer 5 parts by weight of a bisazo dye of formula (A), 2.5 parts by weight of a commercially available butyral resin (Trademark "Denka Butyral Resin #3000-2", made by Denki Kagaku Kogyo K. K.), and 92.5 parts 6 parts by weight of Compound No. 1 prepared in Synthesis Example 1, 10 parts by weight of a polycarbonate resin (Trademark "Panlite K-1300", made by Teijin Limited), 0.002 parts by weight of a methyl phenyl silicone (Trademark "KF50-100cps", made by Shin-Etsu Chemical Co., Ltd.), and 94 parts by weight of tetrahydrofuran were mixed to prepare a coating liquid for a charge transport layer. The thus obtained coating liquid was coated by the doctor blade on the above obtained charge generation layer, and dried, so that a charge transport layer with a thickness of 20.0 μm was formed on the charge generation layer. Thus, a laminate-type electrophotographic photoconductor No. 1 of the present invention comprising an aluminum support, the charge generation layer, and the charge transport layer was obtained.

Examples 2 to 15

The procedure for preparing the electrophotographic photoconductor No. 1 in Example 1 was repeated except that the Compound No. 1 for use in the coating liquid for the charge transport layer in Example 1 was replaced by each of the α-cyanostilbene compounds shown in Table 2, whereby laminate-type electrophotographic photoconductors No. 2 to No. 15 of the present invention were obtained.

Example 16

The procedure for preparing the electrophotographic photoconductor No. 1 in Example 1 was repeated except that 5 parts by weight of the bisazo dye of formula (A) for use in the coating liquid for the charge generation layer used in Example 1 were replaced by 6 parts by weight of a trisazo dye of formula (B), whereby a laminate-type electrophotographic photoconductor No. 16 of the present invention was obtained.

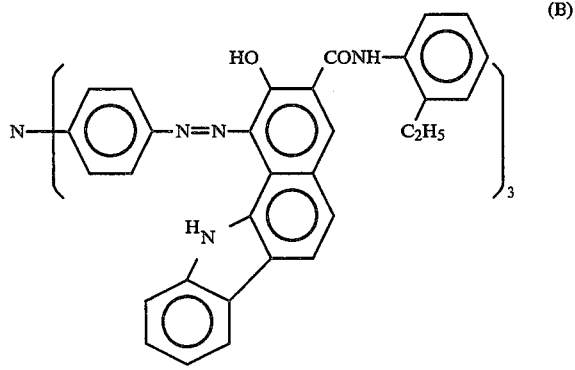

(B)

Examples 17 to 29

The procedure for preparing the electrophotographic photoconductor No. 16 in Example 16 was repeated except that the Compound No. 1 for use in the coating liquid for the charge transport layer used in Example 16 was replaced by each of the α-cyanostilbene compounds shown in Table 2, whereby laminate-type electrophotographic photoconductors No. 17 to No. 29 of the present invention were obtained.

Example 30

Formation of Charge Generation Layer

A mixture of 5 parts by weight of titanylphthalocyanine (TiPc), 5 parts by weight of a polyvinyl butyral resin (Trademark "S-Lec BLS", made by Sekisui Chemical Co., Ltd.), and 90 parts by weight of tetrahydrofuran was dispersed in a ball mill for 12 hours. Tetrahydrofuran was further added to the thus obtained mixture in such an amount that the obtained dispersion might have a concentration of 2 wt. %, and the mixture was dispersed again to prepare a coating liquid for a charge generation layer. The thus obtained coating liquid was coated by a doctor blade on an aluminum-deposited surface of an aluminum-deposited polyester film with a thickness of 100 μm serving as a support, and dried, so that a charge generation layer with a thickness of 0.5 μm was formed on the support.

Formation of Charge Transport Layer 6 parts by weight of Compound No. 1, 10 parts by weight of a polycarbonate resin (Trademark "Panlite K-1300", made by Teijin Limited), and 94 parts by weight of tetrahydrofuran were mixed to prepare a coating liquid for a charge transport layer. The thus obtained coating liquid was coated by the doctor blade on the above obtained charge generation layer, and dried, so that a charge transport layer with a thickness of 20.0 μm was formed on the charge generation layer. Thus, a laminate-type electrophotographic photoconductor No. 30 of the present invention comprising an aluminum support, the charge generation layer, and the charge transport layer was obtained.

Examples 31 to 46

The procedure for preparing the electrophotographic photoconductor No. 30 in Example 30 was repeated except that the Compound No. 1 for use in the coating liquid for the charge transport layer used in Example 30 was replaced by each of the α-cyanostilbene compounds shown in Table 2, whereby laminate-type electrophotographic photoconductors No. 31 to No. 46 of the present invention were obtained.

Each of the thus prepared electrophotographic photoconductors No. 1 to No. 46 according to the present invention was positively charged under application of +6 kV of corona charge, using a commercially available electrostatic copying sheet testing apparatus ("Paper Analyzer Model SP-428", made by Kawaguchi Electro Works Co., Ltd.). Then, each electrophotographic photoconductor was allowed to stand in the dark for 20 seconds without applying any charge thereto, and the surface potential Vo (V) of the photoconductor was measured. Each photoconductor was then illuminated by a tungsten lamp in such a manner that the illuminance on the illuminated surface of the photoconductor was 40 lux, and the exposure $E_{\frac{1}{2}}$(lux·sec) required to reduce the initial surface potential Vo (V) to ½ thereof was measured. The results are shown in Table 2.

TABLE 2

| Example No. | Charge Generating Material | α-cyano-stilbene Compound No. | Vo (V) | $E_{\frac{1}{2}}$ (lux · sec) |
|---|---|---|---|---|
| Ex. 1 | A | 1 | 1335 | 22.9 |
| Ex. 2 | A | 3 | 1411 | 121.4 |
| Ex. 3 | A | 25 | 1906 | 13.8 |
| Ex. 4 | A | 36 | 1881 | 10.5 |
| Ex. 5 | A | 52 | 1730 | 20.3 |
| Ex. 6 | A | 64 | 1933 | 36.4 |
| Ex. 7 | A | 66 | 1382 | 43.8 |
| Ex. 8 | A | 88 | 1509 | 11.0 |
| Ex. 9 | A | 98 | 2071 | 67.8 |
| Ex. 10 | A | 102 | 1917 | 8.6 |
| Ex. 11 | A | 104 | 2019 | 83.4 |
| Ex. 12 | A | 116 | 2051 | 17.2 |
| Ex. 13 | A | 144 | 1400 | 50.4 |
| Ex. 14 | A | 154 | 1465 | 13.8 |
| Ex. 15 | A | 166 | 1400 | 18.4 |
| Ex. 16 | B | 1 | 1250 | 37.1 |
| Ex. 17 | B | 8 | 1142 | 74.2 |

TABLE 2-continued

| Example No. | Charge Generating Material | α-cyano-stilbene Compound No. | Vo (V) | $E_{\frac{1}{2}}$ (lux · sec) |
|---|---|---|---|---|
| Ex. 18 | B | 25 | 1782 | 18.1 |
| Ex. 19 | B | 36 | 1562 | 16.4 |
| Ex. 20 | B | 52 | 1699 | 15.3 |
| Ex. 21 | B | 64 | 1648 | 24.6 |
| Ex. 22 | B | 67 | 1401 | 53.9 |
| Ex. 23 | B | 88 | 1544 | 10.2 |
| Ex. 24 | B | 97 | 2106 | 78.6 |
| Ex. 25 | B | 102 | 1564 | 7.4 |
| Ex. 26 | B | 116 | 1316 | 12.7 |
| Ex. 27 | B | 119 | 1853 | 83.4 |
| Ex. 28 | B | 144 | 1376 | 14.3 |
| Ex. 29 | B | 154 | 702 | 19.1 |
| Ex. 30 | TiPc | 1 | 1238 | 19.3 |
| Ex. 31 | TiPc | 2 | 1423 | 80.9 |
| Ex. 32 | TiPc | 25 | 1587 | 15.7 |
| Ex. 33 | TiPc | 36 | 1381 | 11.7 |
| Ex. 34 | TiPc | 52 | 1209 | 10.1 |
| Ex. 35 | TiPc | 64 | 1368 | 28.4 |
| Ex. 36 | TiPc | 88 | 1246 | 8.7 |
| Ex. 37 | TiPc | 102 | 1423 | 6.6 |
| Ex. 38 | TiPc | 104 | 1802 | 58.9 |
| Ex. 39 | TiPc | 112 | 693 | 94.1 |
| Ex. 40 | TiPc | 116 | 1068 | 10.9 |
| Ex. 41 | TiPc | 118 | 1852 | 75.4 |
| Ex. 42 | TiPc | 144 | 1281 | 16.8 |
| Ex. 43 | TiPc | 147 | 638 | 31.7 |
| Ex. 44 | TiPc | 154 | 756 | 14.9 |
| Ex. 45 | TiPc | 156 | 818 | 26.9 |
| Ex. 46 | TiPc | 157 | 742 | 50.3 |

The α-cyanostilbene compounds used as the charge transporting materials in the photoconductor of the present invention can be prepared by a relatively simple, effective method, and they can be excellently dissolved or dispersed in a binder resin. Furthermore, the α-cyanostilbene compounds can function as charge transporting materials capable of effectively accepting and transporting the electrical charges which are generated in a charge generation layer. Accordingly, the electrophotographic photoconductors comprising the α-cyanostilbene compounds as the charge transporting materials have high photosensitivity and can readily bring about the dark decay.

What is claimed is:

1. An electrophotographic photoconductor comprising:
   i) an electroconductive support; and
   ii) a photoconductive layer formed on said electroconductive support comprising:
      a) a charge generating material; and
      b) a charge transport material consisting of an α-cyano compound of the formula (I):

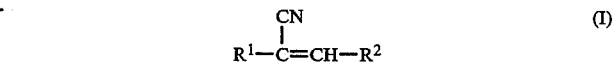

wherein $R^1$ is

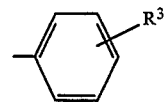

in which $R^3$ is selected from the group consisting of a methyl group, a trifluoromethyl group and chlorine, and $R^2$ is selected from the group consisting of

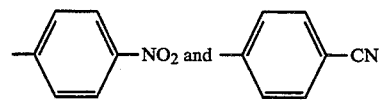

2. The electrophotographic photoconductor of claim 1, wherein said charge transport layer has a thickness of 5 to 50 μm.

3. The electrophotographic photoconductor of claim 1, wherein said charge generation layer has a thickness of 0.1 to 10 μm.

4. The electrophotographic photoconductor of claim 1, wherein said charge generation material is selected from the group consisting of amorphous selenium, trigonal-system selenium, selenium-arsenic alloy, selenium-tellurium alloy, cadmium sulfide, cadmium selenide, cadmium sulfoselenide, mercury sulfide, lead oxide, lead sulfide, amorphous silicone, bisazo dye, polyazo dye, triarylmethane dye, triazine dye, oxazine dye, xanthene dye, cyanine dye, styryl dye, pyrylium dye, quinacridone dye, indigo dye, perylene dye, polycyclic quinone dye, bisbenzimidazole dye, indanthrone dye, squarylium dye, anthraquinone dye and phthalocyanine dye.

5. The electrophotographic photoconductor of claim 1, further comprising a protective layer provided on said photoconductive layer.

6. The electrophotographic photoconductor of claim 1, further comprising an intermediate layer provided between said electroconductive support and said photoconductive layer.

7. The electrophotographic photoconductor of claim 6, wherein said intermediate layer has a thickness of 1 μm or less.

* * * * *